US00PP14861P2

(12) United States Plant Patent
Schräder

(10) Patent No.: US PP14,861 P2
(45) Date of Patent: Jun. 1, 2004

(54) VARIETY OF PETUNIA PLANT NAMED 'SUMPET 08'

(50) Latin Name: *Petunia×atkinsiana*
Varietal Denomination: Sumpet 08

(75) Inventor: Ralf Schräder, Lüdinghausen (DE)

(73) Assignee: Grunewald Veredlings B.V. (NL)

( * ) Notice: Subject to any disclaimer, the term of this patent is extended or adjusted under 35 U.S.C. 154(b) by 0 days.

(21) Appl. No.: 10/378,296

(22) Filed: Mar. 3, 2003

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | | | |
|---|---|---|---|---|---|
| PP12,012 | P2 | * | 7/2001 | Brown | Plt./356 |
| PP13,979 | P3 | * | 7/2003 | Bessho | Plt./356 |
| PP14,286 | P2 | * | 11/2003 | Verwer | Plt./321 |
| 2003/0097698 | P1 | * | 5/2003 | Bessho | Plt./356 |

OTHER PUBLICATIONS

UPOV ROM GTITM Computer Database, GTI JOUVE Retrieval Software 2003/05 Citation for 'Sumpet 08'.*

* cited by examiner

*Primary Examiner*—Bruce R. Campell
*Assistant Examiner*—W C Haas
(74) *Attorney, Agent, or Firm*—Webb Ziesenheim Logsdon Orkin & Hanson, P.C.

(57) ABSTRACT

A new and distinct early flowering Petunia plant with reddish-purple colored flowers.

2 Drawing Sheets

Botanical Cclassification: *Petunia×atkinsiana.*
Varietal denomination: 'Sumpet 08'.

BACKGROUND OF THE INVENTION

The present invention comprises a new and distinct cultivar of Petunia plant known by the varietal name 'Sumpet 08'. The new variety was discovered in May 2001 in a selected breeding program in Lüdinghausen, Germany designed to produce a new variety of Petunia with a hanging character and harmonius habit. The new variety was selected from a cross of proprietary unpatented breeding plants Seedling 96 (female parent) and Seedling 115 (male parent). The new variety is a hanging habitus similar to its parents, but differs in flower color from both parents. The new variety was first asexually reproduced in June 2001 by cuttings in Lüdinghausen, Germany. The new variety has been trial and field tested at Lüdinghausen and has been found to retain its distinctive characteristics and remain true to type through successive propagations.

The following trait distinguishes 'Sumpet 08' as a new and distinct cultivar:

1. Flower color.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
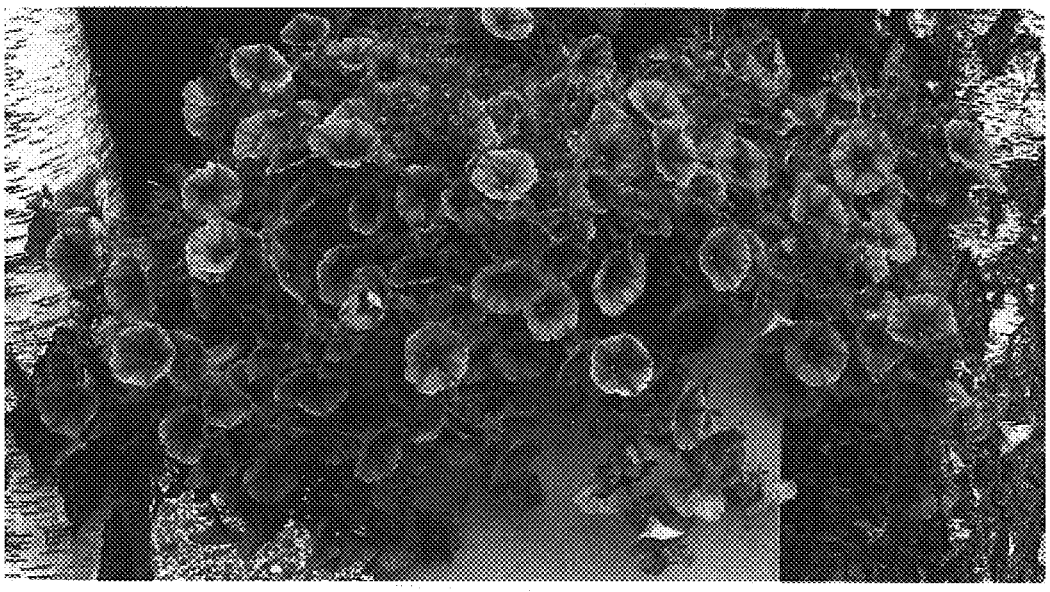
FIG. 1 is a photograph of the plant.
Figure 2:
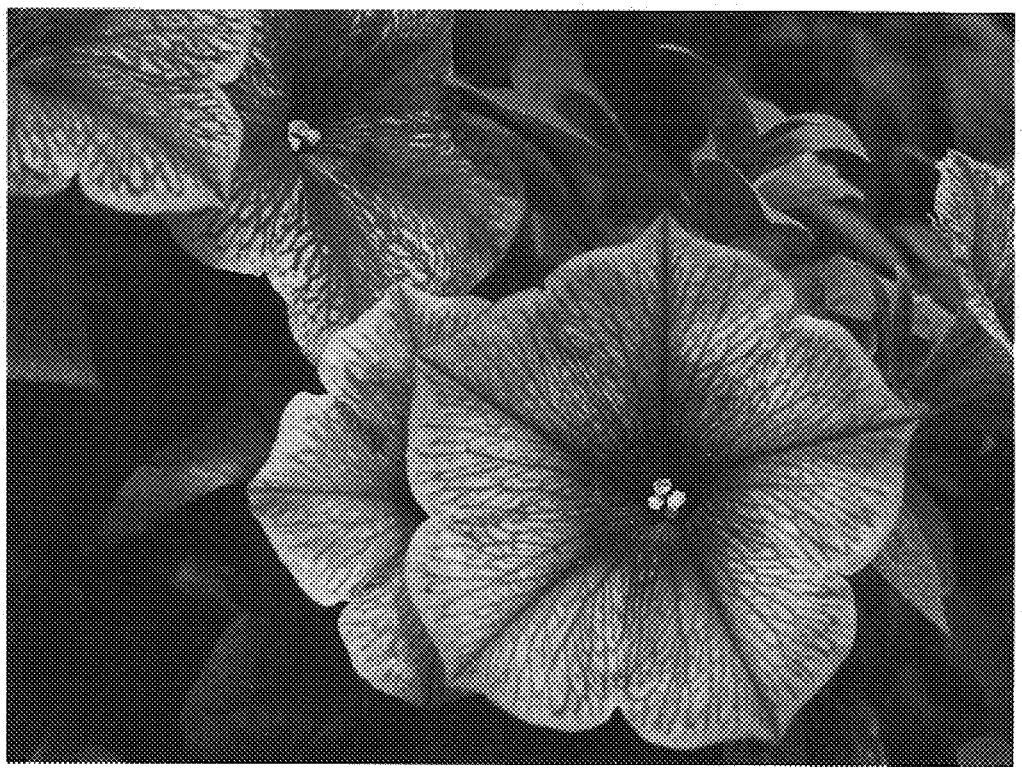
FIG. 2 is a close up view of the blooms of the new plant.

The following detailed description sets forth characteristics of the new cultivar. The data which defines these characteristics were collected by asexual reproductions by cuttings carried out in Lüdinghausen, Germany. Plants for the description were 9 weeks old, grown in a greenhouse in 11 cm containers at 16° C. temperature. The color readings were taken in a greenhouse under natural light. Color references are primarily to The 2001 R.H.S. Colour Chart of The Royal Horticultural Society of London.

PLANT

Form: Spreading.
Height (from soil to top of flowers): 210 mm.
Diameter: 280 mm.
Vigor: Middle.
Roots:
- *Habit.*—Mounded.
- *Time to initiate roots.*—8 days at 18° C.
- *Time to develop roots.*—15 days at 18° C.

Branching habit: Hanging.
Lateral branches:
- *Form.*—Hanging.
- *Color.*—141B.
- *Texture.*—Smooth; heavy; pubescent.
- *Diameter.*—2 mm.
- *Internode length.*—14–16 mm.
- *Quantity.*—8–12.

Foliage:
- *Arrangement.*—Alternate.
- *Number of leaves per branch.*—23.
- *Size of leaf.*—Length: 27 mm. Width: 15 mm.
- *Shape of leaf.*—Lanceolate.
- *Shape of apex.*—Acuminate.
- *Shape of base.*—Acute.
- *Texture.*—Smooth.
- *Margin.*—Entire.
- *Color.*—Young leaves: Lower surface: 146B. Mature leaves: Upper surface: 137A. Lower surface: 146B
- *Petiole.*—Length: 2.5 mm. Diameter: 1.5 mm. Color: 134A.
- Veins—Color: Upper surface: 134A. Lower surface: 134A.

FLOWER

Natural flowering season: Spring to autumn.
Flower type and habit: Simple.
Number of flowers per plant: 12–15.

Corolla:

*Diameter.*—3 mm.

*Flower tube length.*—22 mm.

*Flower tube diameter at distal end.*—16 mm.

*Flower tube diameter at proximal end.*—3 mm.

*Petal length from throat.*—22 mm.

*Petal width.*—26 mm.

*Petal quantity.*—5 parts fused at base.

*Petal apex shape.*—Round.

*Texture.*—Smooth.

*Color.*—When opening: Upper surface: 73A. Lower surface: 68B. Fully opened: Upper surface: 73A. Lower surface: 68B.

*Flower throat* (*inside*).—70B.

*Flower throat, vein.*—59A.

*Flower tube, vein.*—134A.

*Petal color, fading to.*—73A.

Peduncle:

*Length.*——26 mm.

*Diameter.*—1.7 mm.

Color—134A.

*Orientation.*—Angled.

*Strength.*—Middle.

Bud:

*Shape.*—Lanceolate.

*Length.*—24 mm.

*Diameter.*—5 mm.

*Color.*—141A.

Calyx:

*Shape.*—Cuneate.

*Length.*—13 mm.

*Diameter.*—17 mm.

*Sepal shape.*—Lanceolate.

*Sepal margin.*—Entire.

*Sepal texture.*—Smooth.

*Sepal color.*—Upper surface: 137A. Lower surface: 137B.

Disease resistance: No resistance to diseases noted to date.

Fragrance: None.

Weather tolerance: Good.

Lasting quality: Good.

Seed production: Abundant.

REPRODUCTIVE ORGANS

Stamens:

*Number.*—5.

*Filament length.*—9 mm.

*Anthers.*—Shape: Round. Length: 1 mm Color: 130A.

*Pollen.*—Color: 69C. Amount: Abundant.

Pistil:

*Length.*—1 mm.

*Style.*—*Length:* 14 mm. Color: 134B.

*Stigma.*—Shape: Rounded. Color: 140B. Ovary color: 134B.

I claim:

1. A new and distinct variety of Petunia plant substantially as shown and described.

* * * * *